United States Patent [19]
Babu et al.

[11] Patent Number: 5,073,380
[45] Date of Patent: * Dec. 17, 1991

[54] ORAL SUSTAINED RELEASE PHARMACEUTICAL FORMULATION AND PROCESS

[75] Inventors: Suresh R. Babu, Lansdale; Robert Glinecke, Glenside; John L. Murtha, Holland, all of Pa.; Galen W. Radebaugh, Chester, N.J.

[73] Assignee: McNeil-PPC, Inc., Milltown, N.J.

[*] Notice: The portion of the term of this patent subsequent to Apr. 11, 2006 has been disclaimed.

[21] Appl. No.: 549,860

[22] Filed: Jul. 9, 1990

Related U.S. Application Data

[63] Continuation-in-part of Ser. No. 299,178, Jan. 19, 1989, abandoned, which is a continuation-in-part of Ser. No. 78,138, Jul. 27, 1987, Pat. No. 4,820,522.

[51] Int. Cl.$^5$ .............................................. A61K 1/24
[52] U.S. Cl. .................................... 424/472; 424/464; 424/468; 424/469; 424/470; 514/282; 514/80; 514/327; 514/165; 514/569; 514/550; 514/330; 514/716; 514/653; 514/772.5

[58] Field of Search ................................ 424/468, 472

[56] References Cited

U.S. PATENT DOCUMENTS 4,820,522  4/1989  Radebaugh ........................ 424/468

Primary Examiner—Thurman K. Page
Assistant Examiner—D. Gabrielle Phelan
Attorney, Agent, or Firm—Joseph J. Brindisi

[57] ABSTRACT

A pharmaceutical sustained release tablet or tablet layer is formed by making a wet granulation, using povidone (PVP) in water or alcohol-water as the granulating fluid which is mixed with a pharmaceutical active, hydroxyethyl cellulose, a wicking agent e.g. microcrystalline cellulose, then drying and milling the granulation and blending with dry powdered smoothness enhancer, e.g. povidone, erosion promoter, e.g. pregelatinized starch, additional wicking agent, lubricant e.g. magnesium stearate and glidant e.g. silicon dioxide, and compressing the resultant granulation into a tablet with a smooth outer surface, which tablet provides, upon administration, a slow release of the pharmaceutical active.

20 Claims, No Drawings

ORAL SUSTAINED RELEASE PHARMACEUTICAL FORMULATION AND PROCESS

This is a continuation-in-part of U.S.S.N. 299,178 filed Jan. 19, 1989, now abandoned which in turn is a continuation-in-part of U.S.S.N. 78,138, filed July 27, 1987, now U.S. Pat. No. 4,820,522. This invention relates to a sustained release pharmaceutical dosage, and is more particularly concerned with a pharmaceutical active containing matrix formed from granulations of active mixed with inactive powdered excipients Plus hydroxyethyl cellulose (HEC) using an aqueous solution of Povidone U.S.P. (polyvinylpyrrolidone-PVP) as the granulating agent, which granulations are dried, milled, blended with additional amount of PVP to provide a smoother outer surface, and then compressed into a tablet, and to the process of making the pharmaceutical-containing matrix in a manner so that the rate of release of the pharmaceutical can be varied or controlled.

BACKGROUND OF PRESENT INVENTION

It is desirable to extend the dosing interval of many pharmaceuticals while maintaining the initial Plasma concentrations achievable with conventional tablets or caplets. This would provide immediate and extended therapeutic effect and reduce the number of doses necessary, thereby making therapy more convenient. A way to do this has now been found, using the present invention, whereby two tablets or caplets can be formulated to provide both immediate release and sustained release or sustained release alone such that the dosing interval can be extended to at least eight (8) hours. The matrix of the present invention can be used to make sustained release pharmaceutical preparations in compressed tablet form. The matrix materials used are compressed into a shaped tablet form and provide a smooth surface with low Porosity. The term "tablet" as used herein includes tablets of any shape and includes caplets, which are tablets having a capsule shape. The tablets may additionally be coated with a pharmaceutically acceptable coating material or have pharmaceutically acceptable coloring added to the composition prior to compression.

SUMMARY OF THE INVENTION

The present invention, in its process aspect is directed to the process of preparing a pharmaceutical sustained release shaped and compressed tablet characterized by a slow release of the pharmaceutical active upon administration comprising the following steps:
A) forming a granulating agent by dissolving 5-25 parts by weight povidone in water or in an alcohol-water mixture;
B) blending together in parts by weight of the total composition the following ingredients with sufficient water soluble pharmaceutical active to comprise about 66 to 93 percent by weight of the total composition in dry powder form 5-25 parts by weight hydroxyethyl cellulose and 5-25 parts by weight of a wicking agent e.g. microcrystalline cellulose;
C) adding and mixing the granulating agent from Step A to the blended powders from Step B, to form a wet granulation;
D) drying the wet granulation of Step C;
E) milling the dried granulation from Step D;
F) thoroughly blending the milled dried granulation from Step E with the following parts by weight of the total composition of ingredients in dry powder form: 2-15 parts by weight of an outer surface smoothness enhancer selected from the group consisting of povidone, hydroxyethyl cellulose, hydroxypropyl methylcellulose, hydroxypropyl cellulose, ethyl cellulose, and polyethylene glycol, 2-15 parts by weight erosion promoter, e.g. pregeletanized starch, 5-45 parts by weight wicking agent, e.g. microcrystalline cellulose, 0-10 parts by weight lubricant, e.g. magnesium stearate, and 0-5 parts by weight glidant, e.g. silicon dioxide; and
G) compressing the final granulation from Step F into a tablet or tablet layer.

The mixing of the granulating agent and blended powders in Step C is preferably accomplished in a high shear granulator (mixer).

In its product aspect the present invention is directed to a shaped and compressed sustained release therapeutic composition comprising a pharmaceutical active, granulating agent and excipients combined into a matrix, characterized by a smooth outer surface of low porosity and a slow release of the active medicament upon administration, wherein the granulating agent and excipients includes a combination of two polymers, hydroxyethyl cellulose and povidone, and a wicking agent and erosion polymer, as well as an additional amount of an enhancer to provide a smooth outer surface selected from the group consisting of povidone, hydroxyethyl cellulose, hydroxypropyl methylcellulose, hydroxypropyl cellulose, ethyl cellulose, and polyethylene glycol and wherein the total amount of the non-active ingredients in the sustained release matrix is from about 7 to about 34 percent by weight of the tot 1 composition. In more preferred embodiments, the amount of non-active ingredients is less than about fifteen (15) percent of the weight of said shaped and compressed composition.

The preferred tablets of this invention include a shaped and compressed pharmaceutical sustained release tablet made by wet granulating from about 68 to about 94 by weight of the total composition of water soluble active and the excipients ingredients of Part I with the granulating agent of Part II, drying and milling the resultant granulations, and then blending with the excipients of Part III and compressing into a tablet, wherein the ingredients of parts I, II and III comprise the following:

|  | Ingredient | Parts by Weight |
|---|---|---|
| Part I | excipients | |
|  | hydroxyethyl cellulose | 5-25 |
|  | microcrystalline cellulose | 5-25 |
| Part II | granulating agent | |
|  | povidone | 5-25 |
|  | water or alcohol-water | q.s |
| Part III | excipients | |
|  | povidone | 2-15 |
|  | pregelatinized starch | 2-15 |
|  | microcrystalline cellulose | 5-45 |
|  | magnesium stearate | 0-10 |
|  | colloidal silicon dioxide | 0-5 |

The invention preferably is utilized in the form of a bi-layer tablet containing both an immediate release layer and a sustained release layer.

In preferred embodiments of the invention the pharmaceutical active is water soluble and is selected from the group consisting of acetaminophen; codeine; codeine phosphate; loperamide; aspirin; naproxen; propoxyphene HCl; meperidine HCl; dipenhydramine; pseudoephedrine; and any pharmaceutically acceptable salts thereof.

In addition to the hydroxyethyl cellulose and PVP polymers discussed above which are "matrix binding agents", the preferred excipients which are granulated with the active include a "wicking agent" (to wick fluids into the matrix) preferably, microcrystalline cellulose and an effective additional amount of an outer surface smoothness enhancer, preferably, PVP, to provide for a smoother outer surface of the tablet. Additional excipients which are preferably added to the granulated and dried ingredients include an additional amount of a wicking agent, preferably microcrystalline cellulose, an erosion promoter, preferably pregelatinized starch, and preferably a lubricant such as magnesium stearate and optionally a glidant such as colloidal silicon dioxide.

DETAILED DESCRIPTION OF THE INVENTION

The sustained release matrix pharmaceutical tablets of the present invention are made by adding granulating agent to a dry Powder blend of active drug and inactive excipients to form wet granulations, which are then dried and finely divided, e.g. by milling the dried granulations into a finer powder form, then blending with additional inactive powdered excipients including the outer surface smoothness enhancer and compressing into tablets. Tablets can be readily manufactured using conventional tableting equipment.

The tablets of the present invention have novel and advantageous features. A primary advantage is that the tablets are bioerodible when swallowed, that is, no insoluble tablet shaped device remains to be excreted or removed from the body after the active medicament is depleted from the tablet. The sustained release matrix uses hydroxyethyl cellulose (hydroxyethyl cellulose NF) and povidone (povidone USP) (Plasdone ® K29/32) (PVP) as the Matrix Binding Agents for obtaining the sustained release effect.

An important aspect of the present invention is the inclusion as an excipient of an outer surface smoothness enhancer ("Smoothness Enhancer"), which is defined herein as an excipient whose inclusion in effective amounts results in an outer surface of a compressed tablet core which has reduced Porosity and a smoother surface which provides an improved final surface appearance or provides a smoother surface for subsequent coating. This combination of an erosion promoter and wicking agent and a smoothness enhancer in the relative proportions and in the manner used here is believed to be a major novel feature of the present invention.

In the most preferred embodiments of the invention, the amount of hydroxyethyl cellulose and povidone used as matrix binding agents are each on the general order of four percent or less of the amount of active medicament used whereas the amount of smoothness enhancer used is about 0.5 to 3.0% of the amount of active medicament used. This means the sustained release matrix of the present invention is capable of producing dosage forms having very high drug/matrix binding agent ratios. The matrix tablets or tablet layers of the present invention have active drug-to-excipients ratio on the order of 85 percent active to 15 percent excipients by weight. This results in a drug-to-total maxtrix weight ratio of approximately 1:1.2. This results in reducing the size or number of tablets needed, making the product easier to swallow, less expensive and more desirable to the consumer.

Another advantage of this invention is that the rate of matrix erosion when the tablet is swallowed can be modified by altering the levels of excipients, to match a desired blood plasma concentration versus time profile.

The sustained release matrix of the present invention can be used alone as a shaped and compressed tablet (tablet can be any shape such as oval, round, caplet or spherical), or as part of a multi-layered tablet containing an immediate or quick-release layer to elevate the blood levels of active medicament quickly and also containing a sustained release portion to maintain the elevated blood level. Hence, the present invention can be used to prepare tablets with two or more layers, each with a significantly different release rate of the same component, or to prepare tablets of different components where a combination of drugs is desired. As discussed, the hydroxyethyl cellulose and PVP polymers are matrix binding agents. The preferred smoothness enhancer is PVP polymer but other smoothness enhancers include hydroxyethyl cellulose, hydroxypropyl methylcellulose, hydroxypropyl cellulose, ethyl cellulose and polyethylene glycol. Other excipients that are granulated with the active include a wicking agent (to wick fluids into the matrix) such as microcrystalline cellulose. Additional excipients that are added to the granulated and dried ingredients include additional wicking agent such as microcrystalline cellulose, an erosion Promoter such as pregelatinized starch, and preferably a lubricant such as magnesium stearate.

For each of the particular ingredients used in the sustained release matrix of the present invention, aside from the active, the hydroxyethyl cellulose, and the povidone (PVP) there exists less preferred alternative or equivalent materials which could be used instead. The following Table I lists each of the various preferred ingredients, the purpose of the ingredient, the preferred weight of such Preferred ingredient, the usable weight range of the preferred ingredient, other less preferred alternatives or equivalents which can be substituted for the preferred ingredient, the preferred weight of such alternate ingredient and the usable weight range of such alternate ingredient needed for a sustained release layer containing 325 mg of active. For matrices (tablets or caplets) of a higher or lower level of active, the amounts of ingredients and their ranges would be proportionately increased or decreased.

The ingredients are listed in Table I under Part I Active and Excipients, Part II Granulating Agent, Part III Excipients, since they are used in this manner in the process by which the tablets of the present invention are made.

The Preferred process which is utilized to form the most preferred sustained release matrix of the Present invention is to mix together the dry powdered active drug, the dry powdered matrix binding agent, hydroxyethyl cellulose, and the dry powdered wicking agent, microcrystalline cellulose in a mixer/granulator. A granulating fluid or solution is formed by dissolving povidone into water at a ratio of 19.1 grams of povidone to 100 grams of water. The resultant granulating agent is sprayed onto the above admixed powders while they are being mixed in the mixer/granulator so as to form a wet granulation. The wet granulation thus obtained is dried and milled. At this point, the smoothness enhancer e.g. povidone and a small amount of dry powdered excipients such as pregelatinized starch, microcrystalline cellulose and magnesium stearate are added, and mixed with the milled granulations, after which they are compressed thereby forming the sustained release matrix.

The preferred levels of active used in the sustained-release matrix of the invention utilizing the ingredients listed in Table 1 are from about 66 to 93% active medicament ingredient and conversely from about 7 to 34% inactive ingredients by weight of the total composition of the sustained release matrix. This percentage of active versus non-active (granulating agent and excipients) ingredients is consistent with the weight of ingredients given in Table 1. For example, utilizing 325 mg of active and the minimal ranges of non-active ingredients described in Table 1 a total matrix weight of 349 mg is achieved which would be 325/349 or about 93% active, conversely 7% non-active by weight of the total composition. Utilizing 325 mg of active and the maximal ranges of non-active ingredients described in Table 1 a total matrix weight of 490 is achieved which would be 325/490 or about 66% active, conversely 34% non-active by weight of the total composition.

EXAMPLE I

ACETAMINPHEN SUSTAINED RELEASE BI-LAYER TABLET

This example illustrates a bi-layer tablet in which there is both an immediate release layer and a sustained release layer. The immediate release layer is analogous in composition and manufacturing procedure to currently available over-the-counter acetaminophen non-sustained release tablets. It is the sustained release layer that utilizes the matrix of the present invention. The acetaminophen content of the entire tablet is 650 mg. The bi-layer tablet uses the following ingredients:

| Ingredient | mg/Tablet |
|---|---|
| A. Immediate Release Layer | |
| Part I - Active and Excipients | |
| acetaminophen, USP | 325.0 mg |
| powdered cellulose, NF | 42.3 mg |
| pre-gelatinized starch, NF | 16.0 mg |
| Part II - Granulating Agent | |
| starch, NF | 26.0 mg |
| purified water USP | q.s. |
| Part III - Excipients | |
| Sodium laurel sulphate, NF | 0.75 mg |
| magnesium stearate, NF | 2.0 mg |
| Total | 412.05 mg |
| B. Sustained Release Layer | |
| Part I - Active and Excipients | |
| Acetaminophen, USP | 325.0 mg |

TABLE I

SUSTAINED RELEASE ACETAMINOPHEN MATRIX

| Preferred Ingredient | Purpose | (mg) Wt. per Tablet | (mg) Range | Alt. or Equiv. | (mg) Wt. per Tablet | (mg) Range |
|---|---|---|---|---|---|---|
| Part I - Active & Excipients | | | | | | |
| Pharmaceutical Active | Active | 325 | — | — | — | — |
| Hydroxyethyl Cellulose NF (Natrosol*/250L) | Matrix Binding Agent | 10.7 | 5-25 | — | — | — |
| Microcrystalline Cellulose NF, (Avicel* OG k9km k92m k93m k95) | Wicking Agent | 10.7 | 5-25 | Powdered Cellulose (Solka Floc*) | 10.7 | 5-25 |
| Part II - Granulating Agent | | | | | | |
| Povidone, USP (Plasdone* K29/32) | Matrix Binding Agent | 10.7 | 5-25 | — | — | — |
| Purified Water, USP | Solvent | q.s | | water-alcohol (up to 50%) | | |
| Part III - Excipients | | | | | | |
| Povidone, USP | Smoothness enhancer | 5.0 | 2-15 | Hydroxyethyl Cellulose Hydroxypropyl Methylcellulose Hydroxypropyl Cellulose Ethyl Cellulose Propylene Glycol | 5.0 | 2-15 |
| Microcrystalline Cellulose USP (Avicel* PH 101, 103, 103, 103) | Wicking Agent | 15.0 | 5-45 | Powdered Cellulose (Solka Floc*) | 15.0 | 5-45 |
| Pregelatinized Starch, NF (corn, wheat, or potato source) | Erosion Promoter | 5.0 | 2-15 | Starch NF (corn, wheat or potato) or rice starch, Sodium Starch Glycolate NF (Explotab*) Croscarmellose Sodium NF (Ac Di Sol*) Crospovidone NF (PoVIDone*XL) | 5.0 3.0 3.0 3.0 | 5-10 1-10 1-10 1-10 |
| Silicon Dioxide | Glidant | 0.0 | 0-5 | Stearic Acid NF | 5.0 | 5-10 |
| Magnesium Stearate NF | Lubricant | 5.0 | 0-10 | | | |

-continued

| Ingredient | mg/Tablet |
| --- | --- |
| hydroxyethyl cellulose, NF (NATROSOL* 250L) | 10.7 mg |
| microcrystalline cellulose, NF (AVICEL* PH 101) | 10.7 mg |
| Part II - Granulating Agent | |
| povidone, USP PLASDONE* K29/32) | 10.7 mg |
| Purified water, USP | q.s |
| Part III - Excipients | |
| povidone, USP (PLASDONE* K29/32) | 5.0 mg |
| microcrystalline cellulose, USP (AVICEL* PH 101) | 15.0 mg |
| pregelatinized starch, NF STARCH 1500*) | 5.0 mg |
| magnesium Stearate, NF | 5.0 mg |
| Total | 387.1 mg |
| Total Tablet Weight | 799.15 mg |

The above ingredients are utilized to make a bi-layer tablet, by the following working directions:

Working Directions

A. Immediate Release Layer

1. Weigh the components of Part I and add them to the bowl of fluid bed granulator (AEROMATIC). 2. Prepare the granulating agent (Part II) by adding the purified water to a processing tank (approximately 15 grams water for each gram of starch NF). Slowly mix in the starch and heat the mixture until the temperature reaches 82° C.-84° C. 3. With the components of Part I in a heated fluidized state (inlet air temperature 75° C. to 85° C.), spray the granulating agent into the powders. 4. After all the granulating agent has been sprayed, dry the granulated powders to a moisture content of 1.4–1.9% as determined by loss on drying (e.g. Computrac). 5. Sieve the dried granulation (e.g. Glatt Quick Sieve: Stator No. 3, Screen No. 1.5mm, 1000 RPM). Other machines such as Fitzpatrick Commounition Mill can be used.

6. Blend the sieved and dried granulation with the powders of Part III using a suitable mixer such as a twin-shell, ribbon or planetary mixer.

B. Sustained Release Layer

1. Weigh the components of Part I and preblend in a high shear mixer (Fielder: impeller speed of approximately 250 RPM for 1 minute). 2. Prepare the granulating agent (Part II) by dissolving the providone USP in the purified water USP (a ratio of 19.1 grams of povidone to 100 gm of water).

3. Spray the granulating agent at a rate of 400 ml/min onto Part I in the high shear mixer. Granulate the mixture for one minute after the addition of Part II (Fielder: impeller speed of approximately 3000 RPM).

4. Remove the completed wet granulation from the high shear mixer and load it into the product bowl of a fluid bed apparatus (e.g. Aeromatic or Glatt). With an inlet air temperature of approximately 60° C, dry the granulation to a moisture level of 2.0 to 3.0% as determined by loss on drying (e.g. Computrac). The wet granulation can also be dried on trays in drying ovens.

5. Sieve the dried granulation (Glatt Quick Sieve: 1.5mm Screen, Stator, No. 3, 305 RPM). Other machines such as Fitzpatrick Commounition Mill can be used.

6. Blend the sieved and dried granulation with the powders of part III using a suitable mixer such as a twin-shell, ribbon or planetary mixer.

C. Compression of Tablets or Caplets

1. Load the granulation of the immediate release layer into one hopper and the granulation of the sustained release layer into the second hopper of a bi-layer tableting machine (e.g. Stokes Versapress). Compress tablets using 0.749 ×0.281 ×0.060 extra deep concave capsule shaped tooling (Tablet Tooling of other shapes such as oval or round can also be used). The sustained release layer has a target weight of 382.1 mg and the immediate release layer has a target weight of 412.05 mg. Ideal tablet hardness immediately after compression is 10–12 Kp.

The bi-layer tablets of Example I are tested in twelve adult male human subjects and compared to non-sustained release (immediate release only) tablets in a cross-over design. Two tablets of Example I, which contained 1300 mg of acetaminophen, are dosed at time =0 hour. The non-sustained release tablets, each containing 500 mg acetaminophen are dosed as two tablets (1000 mg acetaminophen) also at time =0 hour. Subjects are fasted at least 8 hours prior to administration of the dose. Blood samples are taken from each subject at 0, 1, 1.5, 2, 3, 4, 6, 8, 10 and 12 hours. Plasma is separated from the blood and the concentration of acetaminophen in each sample is determined. The two bi-layer tablets of Example I, when compared to two tablets of non-sustained release acetaminophen (1000 mg dose), achieve the following: comparable rate of absorption; comparable maximum plasma concentration; and comparable extent of absorption (AUC or area under the curve) when adjusted for dose. Theoretically, the 1300 mg dose should provide 130% of the AUC of the 1000 mg dose. Tables 2a and 2b show comparable extents of absorption by the following calculation: (64.3 mcg/ml divided by 49.5 mcg/ml) ×100% =130%.

The tablets of Example I Provide the opportunity to dose 30% more acetaminophen in a more convenient manner by extending the dosing interval to at least eight hours.

TABLE 2a

Sustained Release Acetaminophen 650 mg bi-layer tablets.
(Example I) Average Plasma Concentration Levels of
Acetaminophen (mcg/ml) in twelve subjects after
administering of two tablets (1300 mg). Average AUC
equaled 64.3 mcg/hr.
TIME (HOURS) POST DOSING

| 0 | 1.0 | 1.5 | 2.0 | 3.0 | 4.0 | 6.0 | 8.0 | 10.0 | 12.0 |
| --- | --- | --- | --- | --- | --- | --- | --- | --- | --- |
| | | | | Average (mcg/ml) | | | | | |
| 0 | 12.5 | 12.8 | 11.9 | 10.0 | 7.5 | 4.4 | 2.6 | 1.6 | 1.0 |

TABLE 2b

Non-sustained Release Acetaminophen 500 mg tablets.
Average Plasma Concentration Levels of Acetaminophen
(mcg/ml) in twelve subject. Average AUC equaled 49.5
mcg/hr.
TIME (HOURS) POST DOSING

| 0 | 1.0 | 1.5 | 2.0 | 3.0 | 4.0 | 6.0 | 8.0 | 10.0 | 12.0 |
| --- | --- | --- | --- | --- | --- | --- | --- | --- | --- |
| | | | | Average (mcg/ml) | | | | | |
| 0 | 12.1 | 11.4 | 10.0 | 7.3 | 5.3 | 2.9 | 1.8 | 1.1 | 0.6 |

EXAMPLE II

Acetaminophen Sustained Release Tablet Containing 650 mg of Acetaminophen in Matrix Form This example illustrates an all-matrix (mono-layer) tablet in which there is only a sustained release layer. The working directions are analogous to the working directions for the sustained release layer described in Example I except that the amounts of all ingredients are proportionally increased such that the final tablet contains 650 mg acetaminophen. Tablets can be compressed using capsule, oval, round or other appropriately shaped tooling. The final target weight of the compressed tablet is 764.2 mg.

| Ingredient | mg/Tablet |
|---|---|
| Part I - Active and Excipients | |
| acetaminophen, USP | 650.0 mg |
| hydroxyethyl cellulose, NF (NATROSOL* 250L) | 21.4 mg |
| microcrystalline cellulose, NF (AVICEL* PH 101) | 21.4 mg |
| Part II - Granulating Agent | |
| povidone, USP (PLASDONE* K29/32) | 21.4 mg |
| purified water, USP | q.s |
| Part III - Excipients | |
| povidone, USP (PLASDONE* K29/32) | 5.0 mg |
| microcrystalline cellulose, NF (AVICEL* PH 101) | 30.0 mg |
| pregelatinized starch, NF (STARCH 1500*) | 10.0 mg |
| magnesium stearate, NF | 10.0 mg |
| Total | 769.2 mg |

EXAMPLE III

Acetaminohen/Pseudoephedrine Sustained Release Bi-layer Tablet

This example illustrates a bi-layer tablet which is analagous to the tablet described in Example I, except pseudoephedrine is added to the acetaminophen as a second active ingredient and all amounts of active and non-active ingredients per tablet and final weight of the tablet are proportionally increased.

| Ingredient | mg/Tablet |
|---|---|
| A. Immediate Release Layer | |
| Part I - Active and Excipients | |
| acetaminophen, USP | 333.33 mg |
| pseudoephedrine hydrochloride, USP | 30.00 mg |
| powdered cellulose, NF | 43.4 mg |
| pregelatinized starch, NF | 16.4 mg |
| Part II - Granulating Agent | |
| starch, NF | 26.7 mg |
| purified water, USP | q.s |
| Part III - Excipients | |
| sodium lauryl sulfate, NF | 0.77 mg |
| magnesium stearate, NF | 2.05 mg |
| Total | 452.65 mg |
| B. Sustained Release Layer | |
| Part I - Active and Excipients | |
| acetaminophen, USP | 333.33 mg |
| pseudoephedrine hydrochloride, USP | 30.0 mg |
| hydroxyethyl cellulose, NF (NATROSOL* 250L) | 11.0 mg |
| microcrystalline cellulose, NF (AVICEL* PH 101) | 11.0 mg |
| Part II - Granulating Agent | |
| povidone, USP (PLASDONE* K29/32) | 11.0 mg |
| purified water, USP | q.s |
| Part III - Excipients | |
| povidone, USP (PLASDONE* K29/32) | 8.0 mg |
| microcrystalline cellulose, NF (AVICEL* PH 101) | 15.4 mg |
| pregelatinized starch, NF (STARCH 1500*) | 5.13 mg |
| magnesium stearate, NF | 5.13 mg |
| Total | 429.94 mg |
| Total Tablet Weight | 882.64 mg |

EXAMPLE IV

Aspirin Sustained Release Bi-layer Tablet

This example illustrates a bi-layer tablet which is analogous to the tablet described in Example I, except a lesser amount of aspirin is substituted for acetaminophen and all amounts of ingredients per tablet and final weight of the tablet are proportionally decreased. One practical amount of aspirin would be 250 mg such that the total amount of aspirin in a tablet would be 500 mg. The working directions for the immediate release layer and the sustained release layer are analogous to the working directions described in Example I. Tablets can be compressed using capsule, oval, round or other appropriately shaped tooling. For a tablet containing a total of 500 mg aspirin, he sustained release layer has a target weight of 293.89 mg and the immediate release layer has a target weight of 316.92 mg.

| Ingredient | mg/Tablet |
|---|---|
| A. Immediate Release Layer | |
| Part I - Active and Excipients | |
| aspirin, USP | 250 mg |
| powdered cellulose, NF | 32.5 mg |
| pregelatinized starch, NF | 12.3 mg |
| Part II - Granulating Agent | |
| starch, NF | 20.0 mg |
| purified water, USP | q.s |
| Part III - Excipients | |
| sodium lauryl sulfate, NF | 0.58 mg |
| magnesium stearate, NF | 1.54 mg |
| Total | 316.92 mg |
| B. Sustained Release Layer | |
| Part I - Active and Excipients | |
| aspirin, USP | 250.0 mg |
| hydroxyethyl cellulose, NF (NATROSOL* 250L) | 8.23 mg |
| microcrystalline cellulose, NF (AVICEL* PH 101) | 8.23 mg |
| Part II - Granulating Agent | |
| povidone, USP (PLASDONE* K29/32) | 8.23 mg |
| purified water, USP | q.s |
| Part III - Excipients | |
| povidone, USP (PLASDONE* K29/32) | 6.0 mg |
| microcrystalline cellulose, NF (AVICEL* PH 101) | 11.54 mg |
| pregelatinized starch, NF (STARCH 1500*) | 3.85 mg |
| magnesium stearate, NF | 3.85 mg |
| Total | 299.89 mg |
| Total Tablet Weight | 616.81 mg |

The scope of the present invention is not limited by the description, examples and suggested used herein and modifications can be made without departing from the spirit of the invention. For example, other components may be added to the tablets including additional actives, various flavorings, preservatives and other pharmaceutical excipients. The present invention may also be used to provide sustained release forms for vitamins, minerals or other nutrients.

Application of the compositions and processes of the present invention for medical and Pharmaceutical uses can be accomplished by any clinical, medical and pharmaceutical methods and techniques as are presently and prospectively known to those skilled in the art. Thus it is intended that the present invention cover the modifications and variations of this invention provided that they come within the scope of the appended claims and their equivalents.

What is claimed is:

1. A process of preparing a pharmaceutical-sustained release shaped and compressed tablet characterized by a slow release of pharmaceutical active upon administration comprising the following steps:
   A) forming a granulating agent by dissolving 5-25 parts by weight of the total composition of povidone in water or in an alcohol-water mixture;
   B) blending together, in parts by weight of the total composition, the ,following ingredients, with sufficient water soluble pharmaceutical active to comprise about 66 to 93 percent by weight of the total composition, in dry powder form, 5-25 parts by weight hydroxyethyl cellulose and 5-25 parts by weight of a wicking agent;
   C) adding and mixing the granulating agent from Step A to the blended powders from Step B, to form a wet granulation;
   D) drying the wet granulation of Step C;
   E) milling the dried granulation from Step D;
   F) thoroughly blending the milled dried granulation from Step E with the following parts by weight of the total composition of ingredients in dry powder form: 2-15 parts by weight of a smoothness enhancer, 2-15 parts by weight erosion promoter, 5-45 parts by weight wicking agent, 0-10 parts by weight lubricant and 0-5 parts by weight glidant; and
   G) compressing the final granulation from Step F into a tablet or tablet layer.

2. The process of claim 1 wherein:
   in Step B the wicking agent used is microcrystalline cellulose or powdered cellulose; and
   in Step F the smoothness enhancer is selected from the group consisting of povidone, hydroxyethyl cellulose, hydroxypropyl methylcellulose, hydroxypropyl cellulose, ethyl cellulose, and polyethylene glycol; the erosion promoter used is 2-15 parts by weight of either pregelatinized starch or starch NF or rice starch, or is 1-10 parts by weight of sodium starch glycolate or croscarmellose sodium or crospovidone; the lubricant used is magnesium stearate or stearic acid; and the glidant used is colloidal silicon dioxide or fumed silicon dioxide.

3. The Process of claim 2 wherein:
   in Step A, when any alcohol is used, it is alcohol USP or dehydrated alcohol USP or methyl alcohol USP or isopropyl alcohol USP, and is used in a quantity equal to or less than the water in the alcohol-water mixture.

4. The process of claim 2 wherein:
   in Step A water is used; in Step B the wicking agent used is microcrystalline cellulose; in Step F the smoothness enhancer is povidone and the erosion promoter is pregelatinized starch; and the lubricant used is magnesium stearate.

5. The process of claim 1 wherein the mixing of the granulating agent and blended powders in Step C is carried out in a high shear granulator.

6. A shaped and compressed sustained release therapeutic composition comprising a water soluble pharmaceutical active, a granulating agent and excipients combined into a matrix, characterized by a slow release of the pharmaceutical active upon administration, wherein the granulating agent and excipients comprise hydroxyethyl cellulose, povidone as a granulating agent, a wicking agent, a smoothness enhancer, and an erosion promoter and wherein the total amount of granulating agent and excipients is effective to bind the active in a sustained release solid matrix but is less than about 34 percent and more than about 7 percent of the weight of said shaped and compressed composition.

7. A composition according to claim 6 wherein the wicking agent is microcrystalline cellulose, the smoothness enhancer is selected from the group consisting of povidone, hydroxyethyl cellulose, hydroxypropyl methyl cellulose, hydroxypropyl cellulose, ethylcellulose, and polyethylene glycol; and the erosion promoter is pregelatinized starch.

8. A composition according to claim 6 wherein by parts by weight of the total composition the granulating agent comprises 5-25 parts by weight povidone and the excipients comprise 5-25 parts by weight hydroxyethyl cellulose, 10-70 parts by weight of a wicking agent, 2-15 parts by weight of a smoothness enhancer, 2-15 parts by weight of an erosion promoter, 0-10 parts by weight of a lubricant, and 0-5 parts by weight of a glidant.

9. A composition according to claim 6 wherein by parts by weight of the total composition the granulating agent comprises 5-25 parts by weight of povidone and the excipients comprise 5-25 parts by weight of hydroxyethyl cellulose, 10-70 parts by weight of microcrystalline cellulose, 2-15 Parts by weight of povidone as a smoothness enhancer, 2-15 parts by weight pregelatinized starch, 0-10 Parts by weight magnesium stearate, and 0-5 parts by weight colloidal silicon dioxide.

10. A composition according to claim 6 wherein the total amount of granulating agent and excipients is greater than about but less than 15 percent of the total weight of said shaped and compressed composition.

11. A composition according to claim 6 wherein the pharmaceutical active is selected from the group consisting of codeine; codeine phosphate; loperamide; aspirin; naproxen; propoxyphene HCl; meperidine HCl; diphenhydramine; pseudoephedrine; and any pharmaceutically acceptable salts thereof.

12. A process of preparing sustained release bi-layer medicament tablet comprising a first layer of immediate release and a second layer of sustained slow release of medicament according to the steps of:
   A) preparing an immediate release layer comprising a water soluble pharmaceutically acceptable excipients; and
   B) Preparing a sustained release layer comprising a medicament water soluble as the active ingredient according to the steps of:

1) forming a granulating agent by dissolving about 5-25 parts by weight of the total sustained release layer of povidone in alcohol or an alcohol-water mixture;
2) blending together a sufficient amount of medicament to comprise 68 to 94 percent of the total weight of the sustained release layer with the following ingredients in dry powder form in parts by weight of the total sustained release layer as indicated:

| Ingredient | Parts by Weight |
|---|---|
| hydroxyethyl cellulose | 5-25 |
| wicking agent | 5-25; |

3) adding the granulating agent from Step 1 to the blended powders from Step 2, and forming a wet granulation;
4) drying the wet granulation of Step 3;
5) milling the dried granulation Step 4;
6) thoroughly blending the milled dried granulation from Step 5 with the following ingredients in dry powder form;

| Ingredient | Parts by Weight |
|---|---|
| smoothness enhancer | 2-15 |
| erosion promoter | 2-15 |
| wicking agent | 5-45 |
| lubricant | 0-10 |
| glidant | 0-5; and |

C) combining and compressing the immediate release layer of Step A with the sustained release layer of Step B into a bi-layered tablet.

13. A shaped and compressed bi-layer therapeutic composition comprising a water soluble medicament in a first immediate release layer and a medicament in a second sustained release layer wherein the immediate release layer comprises a medicament and pharmaceutically acceptable excipients and the sustained release layer comprises a medicament, a granulating agent and excipients combined into a matrix, wherein the granulating agent and excipients of the sustained release layer include hydroxyethyl cellulose, povidone as a granulating agent, a wicking agent, a smoothness enhancer, and an erosion promoter and wherein the total amount of said granulating agent and excipients is effective to bind the acetaminophen in a sustained release solid matrix but is less than bout 34 percent of the weight of the sustained release layer of said shaped and compressed bi-layer composition.

14. The therapeutic composition of claim 13 wherein the immediate release layer comprises a medicament which is the same as the medicament in the immediate release layer.

15. The therapeutic composition of claim 13 wherein the amount of granulating agent and excipients is greater than about 7 percent but less than about 15 percent of the total weight of the sustained release layer of said shaped and compressed bi-layer composition.

16. The therapeutic composition of claim 13 wherein the smoothness enhancer is selected from the group consisting of povidone, hydroxyethyl cellulose, hydroxypropyl methylcellulose, hydroxypropyl cellulose, ethyl cellulose or polyethylene glycol.

17. The therapeutic composition of claim 13 wherein the wicking agent is microcrystalline cellulose, the smoothness enhancer is povidone and the erosion promoter is pregelatinized starch.

18. A shaped and compressed bi-layered immediate release layer and sustained release layer medicament tablet made by combining an immediate release layer comprising one or medicaments and pharmaceutically acceptable excipients with a sustained release layer made by wet granulating a sufficient amount of one or more water soluble medicaments to comprise 66 to 93 percent of the total weight of the sustained release layer with the Excipients of Part I and the Granulating Agent of Part II, drying and milling the resultant granulations, and then blending with the Excipients of Part III and compressing the two layers into a tablet, wherein the ingredients of Parts I, II and III comprise the following:

| | Ingredient | Range of Parts by Weight of the Total Sustained Release Layer |
|---|---|---|
| Part I | Excipients | |
| | Hydroxyethyl Cellulose | 5-25 |
| | Microcrystalline Cellulose | 5-25 |
| Part II | Granulating Agent | |
| | Povidone | 5-25 |
| | Alcohol or Alcohol-Water | q.s. |
| Part III | Excipients | |
| | Povidone | 2-15 |
| | Pregelatinized Starch | 2-15 |
| | Microcrystalline Cellulose | 5-45 |
| | Magnesium Stearate | 0-10 |
| | Colloidal Silicon Dioxide | 0-5 |

19. A product made by the process of claim 1.
20. A product made by the process of claim 12.

* * * * *

UNITED STATES PATENT AND TRADEMARK OFFICE
CERTIFICATE OF CORRECTION

PATENT NO. : 5,073,380
DATED : December 17, 1991
INVENTOR(S) : Suresh R. Babu, et. al.

It is certified that error appears in the above-indentified patent and that said Letters Patent is hereby corrected as shown below:

Column 12, Claim 10, line 50, "about but less", should read --about 7 but less--.

Column 12, Claim 12, line 66 "medicament water soluble", should read-- water soluble medicament--.

Signed and Sealed this

Nineteenth Day of October, 1993

Attest:

BRUCE LEHMAN

Attesting Officer

Commissioner of Patents and Trademarks